United States Patent
Shalyt et al.

(10) Patent No.: US 9,274,079 B2
(45) Date of Patent: Mar. 1, 2016

(54) ETCHANT PRODUCT ANALYSIS IN ALKALINE ETCHANT SOLUTIONS

(71) Applicants: Eugene Shalyt, Washington Township, NJ (US); Guang Liang, Elmhurst, NY (US); Peter Bratin, Flushing, NY (US)

(72) Inventors: Eugene Shalyt, Washington Township, NJ (US); Guang Liang, Elmhurst, NY (US); Peter Bratin, Flushing, NY (US)

(73) Assignee: ECI Technology, Inc., Totowa, NJ (US)

( * ) Notice: Subject to any disclaimer, the term of this patent is extended or adjusted under 35 U.S.C. 154(b) by 354 days.

(21) Appl. No.: 13/942,412

(22) Filed: Jul. 15, 2013

(65) Prior Publication Data

US 2014/0206090 A1    Jul. 24, 2014

Related U.S. Application Data

(60) Provisional application No. 61/849,274, filed on Jan. 22, 2013.

(51) Int. Cl.
*G01N 27/333* (2006.01)
*G01N 27/416* (2006.01)

(52) U.S. Cl.
CPC .......... *G01N 27/333* (2013.01); *G01N 27/4166* (2013.01)

(58) Field of Classification Search
CPC ........................ G01N 27/333; G01N 27/4166
See application file for complete search history.

(56) References Cited

U.S. PATENT DOCUMENTS

| 8,008,087 B1 * | 8/2011 | Shalyt | G01N 27/4166 436/124 |
| 2004/0108297 A1 * | 6/2004 | Erk | H01L 21/30608 216/2 |

* cited by examiner

*Primary Examiner* — Lyle Alexander
*Assistant Examiner* — Dwan A Gerido
(74) *Attorney, Agent, or Firm* — D. Morgan Tench

(57) ABSTRACT

Silicon ions in an alkaline etchant solution are analyzed by acidifying a sample of the etchant solution, adding fluoride ions in excess of the concentration required to react with all of the silicon ions, and using a fluoride ion specific electrode (FISE) to detect free fluoride ions in the resulting test solution. Good sensitivity and precision are provided by using a relatively acidic test solution and only a slight excess of fluoride ions, and limiting the analysis range to the maximum expected silicon concentration in the etchant solution.

14 Claims, 6 Drawing Sheets

US 9,274,079 B2

ETCHANT PRODUCT ANALYSIS IN ALKALINE ETCHANT SOLUTIONS

CROSS-REFERENCE TO RELATED APPLICATIONS

This application claims priority to U.S. Provisional Patent Application No. 61/849,274 to Shalyt et al. filed 22 Jan. 2013, which is assigned to the same assignee.

BACKGROUND OF THE INVENTION

1. Field of the Invention

This invention is concerned with analysis of semiconductor processing solutions, particularly with determination of the silicon, germanium or titanium concentration in alkaline etchant solutions.

2. Description of the Related Art

Alkaline etchant solutions are widely-used in important industrial processes to provide anisotropic (pyramidal) etching of single-crystal silicon needed for fabrication of high-speed integrated circuit (IC) chips with copper circuitry, efficient solar cells based on nano-technology, and micro-electro-mechanical systems (MEMS) devices, such as accelerometers used in automotive air bag systems. To provide the precise nano-scale silicon features required for such applications, it is necessary to precisely control the silicon etch rate, which tends to decrease as silicon etchant products build up in the etchant solution. A means of accurately measuring the concentration of silicon etchant products in alkaline etchant solutions is needed to allow the etch time to be adjusted as the etch rate changes, and the etchant solution to be replaced based on need rather than a schedule. Conventional methods for detecting silicon ions in solution based on near-infrared (NIR) spectroscopy or ion chromatography (IC) do not provide the sensitivity needed.

Alkaline etchant solutions are also used to etch other materials in industrial manufacturing processes. For example, germanium is increasingly used as a replacement for silicon in semiconductor devices and an improved method of measuring the concentration of germanium ions in alkaline etchant solutions is also needed. As a further example, titanium sputtered onto the source and drain zones of silicon transistors is heated to form TiSi, which provides an ohmic electrical contact to the doped silicon in these zones. An alkaline etchant is used to remove unreacted titanium from the transistor. A suitable method for detecting titanium ions in alkaline etchant solutions is also needed.

U.S. Pat. No. 8,008,087 to Shalyt et al. describes a method for detecting low concentrations of silicon ions in a semiconductor etchant solution by adding a predetermined concentration of fluoride ions to a test solution comprising a predetermined volume of the etchant solution, and measuring the concentration of fluoride ions in the test solution. Reaction with silicon ions in the test solution reduced the concentration of fluoride ions, which were present in stoichiometric excess, so that the silicon concentration of the etchant solution could be calculated from the difference between the predetermined and measured concentrations of fluoride ions in the test solution. This prior art method was successfully applied to analysis of silicon ions in silicon nitride etchants comprising a high concentration of phosphoric acid but cannot be applied directly for analysis of alkaline etchant solutions since fluoride does not react with silicon ions in alkaline solutions.

SUMMARY OF THE INVENTION

The invention provides a method and an apparatus for determining the concentration of an etchant product in an alkaline etchant solution comprising a predetermined concentration of a hydroxide compound dissolved in water. The invention is particularly useful for determining the silicon concentration in alkaline etchant solutions of the type used industrially to provide the anisotropic etching of single-crystal silicon needed for fabrication of high-speed integrated circuit (IC) chips, efficient solar cells and micro-electro-mechanical systems (MEMS) devices. The invention may also be applied to determine the germanium concentration in alkaline etchant solutions of the type used to provide anisotropic etching of germanium for applications analogous to those for silicon. In addition, the invention may be applied to determine the titanium concentration in alkaline etchant solutions of the type used to remove residual titanium from transistors and other semiconductor devices. For ease of discussion, the description of the invention in this document focuses on determination of the silicon concentration in an alkaline etchant solution.

In the method of the invention for determining the silicon concentration in an alkaline etchant solution, a fluoride ion specific electrode (FISE) is used to detect free fluoride ions in a test solution comprising a predetermined volume of the alkaline etchant solution, an acid (phosphoric acid, for example) added at a predetermined concentration to provide a test solution having a pH in the 0.0-3.0 pH range (preferably in the 0.0-2.0 pH range), and fluoride ions added at a predetermined concentration in stoichiometric excess of that required to react with all of the silicon ions in the predetermined volume of an alkaline etchant solution having the maximum expected silicon concentration. In the acidic test solution, silicon exists primarily as the protonated $HSiO_3^-$ and $H_2SiO_3$ species, which react with fluoride ions to form the hexafluorosilicic ion ($SiF_6^{2-}$), which is not detected by the FISE. The difference between the predetermined concentration of fluoride ions added to the test solution and the concentration of free fluoride ions detected by the FISE provides a measure of the silicon concentration in the test solution, which can be used to calculate the silicon concentration in the alkaline etchant solution.

A calibration curve generated under optimum measurement conditions is needed to provide good sensitivity and precision for the analysis of the invention. In particular, the test and calibration solutions should be highly acidic (pH 0.0-3.0), the upper limit of the silicon analysis range should correspond to the maximum expected silicon concentration in the alkaline etchant solution, and the fluoride concentration in the test and calibration solutions should be only slightly in excess of that required to react with all of the silicon ions at the maximum expected concentration in the alkaline etchant solution.

The apparatus of the invention enables automated application of the method of the invention for on-line determination of the silicon concentration in an alkaline etchant solution comprising a hydroxide compound dissolved in water. A basic apparatus of the invention comprises: an analysis cell; a reagent solution comprising predetermined concentrations of an acid and fluoride ions; a means of providing a test solution comprising predetermined volume fractions of the alkaline etchant solution and the reagent solution; a fluoride ion specific electrode (FISE) and a reference electrode in contact with the test solution and electrically connected to a voltmeter; and a computing device having a memory element with a stored algorithm operative to effect, via appropriate interfacing, at least the basic steps of the method of the invention, comprising, providing the test solution in the analysis cell, measuring the potential of the FISE in contact with the test solution, and determining the concentration of the etchant product in the alkaline etchant solution by comparing the potential measured for the FISE in the test solution with a calibration curve.

By enabling accurate, rapid and cost-effective determination of the silicon or germanium concentration in alkaline etchant solutions, the invention is useful for reducing the costs and improving the quality and yield of semiconductor IC chips, solar cells and MEMS devices. The invention may also be applied to determine the titanium concentration in alkaline etchant solutions used for removing residual titanium from semiconductor transistor devices. The steps of the method of the invention are simple to perform, involving standard addition of an acid and a fluoride compound to a sample of the etchant solution and measurement of the fluoride ion concentration in the resulting test solution via a fluoride ion specific electrode (ISE). The invention enables the etch time for an alkaline etchant solution to be adjusted to accurately take into account the effect of the etchant product on the etch rate. Accurate measurement of the etchant product concentration in an alkaline etchant solution according to the invention also enables the etchant solution to be replaced based on need rather than a time schedule so as to minimize down time, costs and the amount of waste generated. The apparatus of the invention is simple and inexpensive, and provides automated analysis according to the method of the invention.

Further features and advantages of the invention will be apparent to those skilled in the art from the following detailed description, taken together with the accompanying drawings.

DETAILED DESCRIPTION OF THE INVENTION

Figure 1:
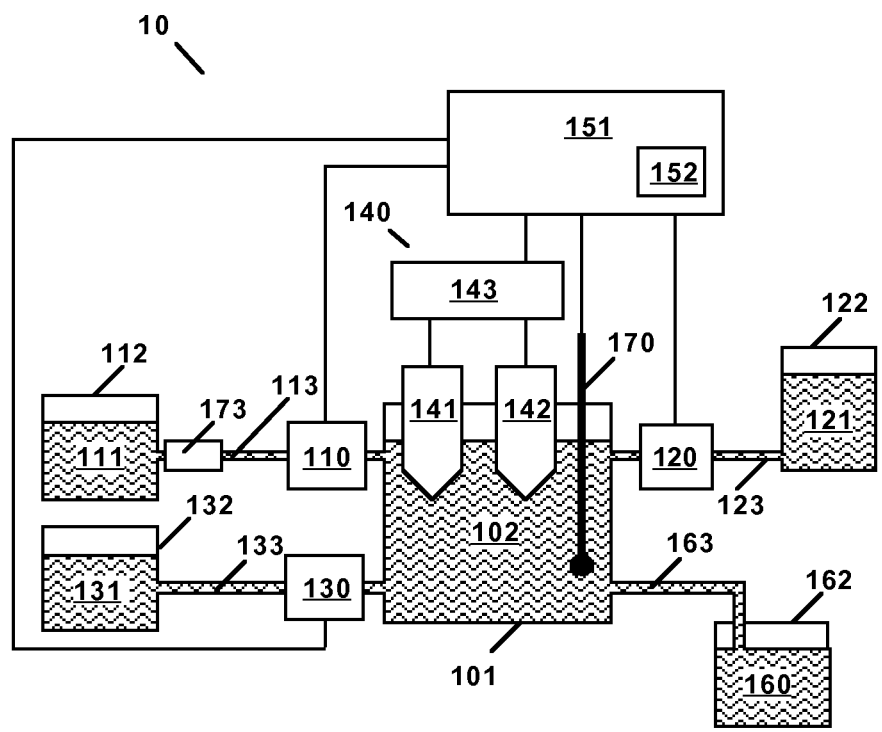
FIG. 1 schematically illustrates a preferred apparatus of the invention for determining an etchant product concentration in an alkaline etchant solution.

Technical terms used in this document are generally known to those skilled in the art. The term "standard addition" generally means addition of a predetermined quantity of a species to a predetermined volume of a solution (a test solution, for example). The predetermined quantity may be a predetermined weight of the species or a predetermined volume of a standard solution containing the species. A "standard solution" comprises a precisely known concentration of an analyzed species or a reagent used for a chemical analysis. The symbol "M" means molar concentration. Calibration data are typically handled as calibration curves or plots but such data may be tabulated and used directly, especially by a computer, and the terms "curve" or "plot" include tabulated data. Water used for solution preparation or dilution is preferably substantially pure water, deionized or distilled water, for example.

It is understood by those skilled in the art that silicon is present in aqueous solutions in ionic form, the fundamental species being the silicate ion ($SiO_3^{2-}$) which tends to exist as the protonated species $HSiO_3^-$ and $H_2SiO_3$ in acidic solutions. However, since silicon forms a variety of complexes and the exact species formed by dissolution of silicon in an alkaline etchant solution are not generally known, the terms "silicon" and "silicon ions" encompass all silicon ions in a solution, and the term "silicon concentration" denotes the total concentration of silicon in all silicon ions in the solution expressed in parts per million (ppm) of silicon (silicon weight in mg per kg of solution). The analogous terms also apply to germanium and titanium etchant products.

The invention provides a method and an apparatus for determining the concentration of an etchant product in an alkaline etchant solution comprising a predetermined concentration of a hydroxide compound dissolved in water. The invention is particularly useful for determining the silicon concentration in alkaline etchant solutions of the type used industrially to provide the anisotropic etching of single-crystal silicon needed for fabrication of high-speed integrated circuit (IC) chips, efficient solar cells and micro-electro-mechanical systems (MEMS) devices. For ease of discussion, the description of the invention in this document focuses on determination of the silicon concentration in an alkaline etchant solution. The invention may also be used to determine the germanium or titanium concentration in alkaline etchant solutions.

In the method of the invention for determining the silicon concentration in an alkaline etchant solution, a fluoride ion specific electrode (FISE) is used to detect free fluoride ions in a test solution comprising a predetermined volume of the alkaline etchant solution, an acid (phosphoric acid, for example) added at a predetermined concentration to provide a test solution having a pH in the 0.0-3.0 pH range, and fluoride ions added at a predetermined concentration in stoichiometric excess of that required to react with all of the silicon ions in the predetermined volume of an alkaline etchant solution having the maximum expected silicon concentration.

It is necessary that the test solution be acidic since silicon exists in alkaline solutions as the silicate ion ($SiO_3^{2-}$), which does not react with free fluoride ions. In the acidic test solution, silicon exists primarily as the protonated $HSiO_3^-$ and $H_2SiO_3$ species, which react with fluoride ions to form the hexafluorosilicic ion ($SiF_6^{2-}$), which is not detected by the FISE. The difference between the predetermined concentration of fluoride ions added to the test solution and the concentration of free fluoride ions detected by the FISE provides a measure of the silicon concentration in the test solution, which can be used to calculate the silicon concentration in the alkaline etchant solution.

Since the concentration of free fluoride ions in the test solution is affected by complicated pH-dependent equilibria involving HF and various fluorine-containing ions, including hexafluorosilicic ion ($SiF_6^{2-}$), a calibration curve generated under optimum measurement conditions is needed to provide good sensitivity and precision for the analysis of the invention. Optimum measurement conditions include, a relatively acidic test solution, only a slight excess of fluoride ions, and an analysis range limited to the maximum expected silicon concentration in the alkaline etchant solution.

Generation of the calibration curve preferably involves preparation of a plurality of standard solutions comprising the predetermined concentration of the hydroxide compound and different predetermined silicon ion concentrations in the range from zero to a maximum expected concentration of silicon ions in the alkaline etchant solution. Predetermined concentrations of the acid and fluoride ions are added to each of the standard solutions to provide a plurality of calibration solutions having a pH in the 0.0-3.0 pH range and a concentration of fluoride ions in stoichiometric excess of that required to react with all of the silicon ions in a standard solution having the maximum concentration of silicon ions expected in the alkaline etchant solution. A strongly acidic test solution is needed so that neutralization of the amount of hydroxide from the alkaline etchant solution, which may vary as a function of time, does not substantially change the pH of the test solution. The predetermined concentration of fluoride ions added to calibration and test solutions should be only slightly in excess of that required to react with all of the silicon ions at the maximum expected concentration in the alkaline etchant solution.

The method of the invention for determining the concentration of an etchant product in an alkaline etchant solution comprising a predetermined concentration of a hydroxide compound dissolved in water, comprises the steps of: (1) defining a maximum expected concentration of the etchant product in the alkaline etchant solution; (2) providing a plurality of standard solutions comprising the predetermined concentration of the hydroxide compound and different predetermined concentrations of the etchant product in the range from zero to a maximum expected concentration of the etchant product in the alkaline etchant solution; (3) adding predetermined concentrations of an acid and fluoride ions to each of the standard solutions to provide a plurality of calibration solutions having a pH in the 0.0-3.0 range and a concentration of fluoride ions in stoichiometric excess of that required to react with all of the etchant product in an alkaline etchant solution comprising the maximum expected concentration of the etchant product; (4) generating a calibration curve of a concentration of the etchant product versus the potential of a fluoride ion specific electrode (FISE) by sequentially placing the FISE and a reference electrode in contact with each calibration solution and measuring the potential of the FISE relative to the reference electrode via a voltmeter; (5) providing a test solution comprising a predetermined volume of the alkaline etchant solution and the same predetermined concentrations of the acid and fluoride ions as in the calibration solutions; (6) placing the FISE and the reference electrode in contact with the test solution and measuring the potential of the FISE relative to the reference electrode via the voltmeter; and (7) comparing the potential of the FISE measured for the test solution with the calibration curve to determine the concentration of the etchant product in the alkaline etchant solution. The alkaline etchant solution analyzed by the invention may comprise any suitable hydroxide compound, including tetramethylammonium hydroxide (TMAH), tetraethylammonium hydroxide (TEAH), tetrapropylammonium hydroxide (TPAH), tetrabuytlammonium hydroxide (TBAH), NaOH, KOH and mixtures thereof. Etchant products that may be analyzed by the invention include silicon, germanium and titanium ions.

With respect to Step (1), the maximum expected concentration of the etchant product in an alkaline etchant solution may be defined based on measurements of the etchant product concentration in a production alkaline etchant solution as a function of time. Such measurements may be made by any suitable prior art method, or by the method of the invention using an iterative process involving variation of the predetermined concentration of fluoride ions in the calibration and test solutions. Typically, a process control document (generated by a user or provided by a supplier of the alkaline etchant solution) specifies a maximum allowable concentration of the etchant product, which defines the maximum expected concentration of the etchant product.

With respect to Step (3), the predetermined concentration of the acid added to the calibration solutions (and the test solution) is preferably sufficiently high that the pH of the solutions remains substantially constant despite neutralization of some of the acid by reaction with the hydroxide compound. Preferably, the pH of the test solution and the calibration solutions is in the 0.0 to 2.0 pH range. However, for analysis of some etchant solutions, particularly those having a lower hydroxide concentration, a higher pH for the test and calibration solutions (up to pH 3.0) may be used. Any suitable acid may be used, including one selected from the group consisting of phosphoric acid, sulfuric acid, nitric acid, acetic acid, hydrochloric acid and mixtures thereof.

Also with respect to Step (3), the stoichiometric excess of fluoride ions is preferably less than 30% of the fluoride ion concentration required to react with all of the etchant product in an alkaline etchant solution comprising the maximum expected concentration of the etchant product. For larger excesses of fluoride ions, a small change in the fluoride concentration produces a smaller change in the potential of the FISE, reducing the sensitivity of the alkaline etchant analysis of the invention. In an alkaline etchant solution used to etch silicon, the etchant product is silicate ion ($SiO_3^{2-}$), which requires reaction with six fluoride ions to produce the hexafluorosilicic ion ($SiF_6^{2-}$). In this case, the molar concentration of fluoride ions must be more than six times the molar concentration of the $SiO_3^{2-}$ etchant product.

Also with respect to Step (3), the fluoride ions may be added to the test solution and the calibration solutions as part of any suitable fluoride compound, including those selected from the group consisting of HF, LiF, NaF, KF, $NH_4HF_2$, $NH_4F$, and mixtures thereof. The fluoride compound may be added to the test solution and the calibration solutions as part of a solid compound of known weight, or as a predetermined volume of a standard fluoride solution.

With respect to Step (4), the calibration curve may provide the etchant product concentration in the test solution or in the alkaline etchant solution. The FISE and the reference electrode may be separate electrodes or may be combined in a combination electrode. Any suitable voltmeter may be used.

With respect to Step (5), the predetermined volume of the alkaline etchant solution may be provided manually, using a syringe, a volumetric flask or a graduated cylinder, for example, or automatically, via an automatic syringe or a metering pump, for example.

With respect to Step (7), the free fluoride ion concentration may be determined from the FISE potential measured for each of the calibration solutions and the test solution and used to calculate the concentration of the etchant product. For silicon, the product of the reaction between silicon ions and fluoride ions is assumed to be the hexafluorosilicic ion ($SiF_6^{2-}$) formed by the overall reaction:

$$H_2SiO_3 + 6HF = H_2SiF_6 + 3H_2O$$

involving the dissociated HF species. Under ideal conditions, the potential (E) of a fluoride ISE is given by the well-known Nernst equation:

$$E = E_o - (2.303\, RT/nF) \log [F^-] \qquad (2)$$

where $E_o$ is the standard equilibrium potential, R is the natural gas constant, T is the temperature (° K), n is the number of electrons transferred in the electrode reaction, F is the faraday constant, and $[F^-]$ is the activity of fluoride ions. The value of 2.303 RT/nF is 59 mV/decade for a one-electron reaction at 25° C.

With respect to Step (7), as an alternative, the FISE potentials measured for the test solution and calibration solutions may be converted to free fluoride ion concentrations, which can be used to calculate the concentration of the etchant product in the alkaline etchant solution.

In a preferred embodiment, the predetermined concentrations of the acid and fluoride ions are added to the calibration solutions and the test solution as part of a reagent solution comprising a predetermined concentration of the acid and a predetermined concentration of fluoride ions.

The method of the invention for determining the concentration of an etchant product in an alkaline etchant solution comprising a predetermined concentration of a hydroxide compound dissolved in water, may further comprise the steps of: (8) maintaining the temperature of the calibration solutions substantially constant at a predetermined calibration temperature during FISE potential measurements for the calibration solutions; (9) measuring the temperature of the test solution at the time the FISE potential is measured for the test solution; and (10) correcting the potential measured for the FISE in the test solution for the effect of the difference in the temperature measured for the test solution and the predetermined calibration temperature. The FISE potential may be corrected for a difference in temperature using the Nernst equation (paragraph [0031], equation 2). Means of measuring and controlling the temperature of an electrochemical cell are well-known in the art.

FIG. 1 schematically illustrates a preferred apparatus 10 of the invention for determining the concentration an etchant product in an alkaline etchant solution 111 comprising a hydroxide compound dissolved in water, comprising: (1) a reagent solution 131 comprising predetermined concentrations of an acid and fluoride ions; (2) an analysis cell 101 containing a test solution 102 comprising a predetermined volume of etchant solution 111 and a predetermined volume of a reagent solution 131; (3) a sampling device 110 operative to provide metered flow of alkaline etchant solution 111 from an etchant container 112 or a production processing tank to analysis cell 101 so as to provide a predetermined volume of alkaline etchant solution 111 in test solution 102; (4) a reagent device 130 operative to provide metered flow of reagent solution 131 from reagent reservoir 132 to the analysis cell 101 so as to provide a predetermined volume of reagent solution 131 in test solution 102; (5) a means 140 of measuring the fluoride concentration in test solution 102, comprising fluoride ion specific electrode 141 and a reference electrode 142 in contact with test solution 102 and electrically connected to a voltmeter 143; (6) and a computing device 151 having a memory element 152 with a stored algorithm operative to effect, via appropriate interfacing, at least the basic steps of the method of the invention, comprising (a) providing test solution 102 in the analysis cell 101, (b) measuring the potential of fluoride ion specific electrode 141 relative to reference electrode 142, and (c) determining the concentration of the etchant product in alkaline etchant solution 111 by comparing the potential measured for fluoride ion specific electrode 141 in the test solution with a calibration curve.

The stored algorithm of memory element 152 may also be operative to generate the calibration curve, or a calibration curve from another source (manually or automatically generated) may be used. Preferably, calibrations and analyses are performed automatically using the same apparatus.

Analysis cell 101 may be of any suitable shape, including an open beaker or a closed cell with feedthroughs for the electrodes (as shown in FIG. 1), for example, and may comprise any suitable material, glass or a polyolefin plastic, for example. A preferred analysis cell comprises a jacket through which a heat exchange liquid is passed to control the temperature of test solution 102.

Sampling device 110 for providing a predetermined volume of etchant solution 111 from etchant container 112 to test solution 102 in analysis cell 101 preferably comprises an automatic syringe or a metering pump with associated plumbing and wiring to provide automatic delivery (as indicated in FIG. 1). Etchant container 112 may be a production etchant tank or an etchant reservoir. For automatic delivery of etchant solution 111, sampling device 110 is connected to a pipe 113 running between etchant container 112 and analysis cell 101.

For delivering a predetermined volume of reagent solution 131 from reagent reservoir 132 to test solution 102 in analysis cell 101, reagent device 130 preferably comprises an automatic syringe or a metering pump with associated plumbing and wiring to provide automatic delivery. For automatic delivery of reagent solution 131, reagent device 130 is connected to a pipe 133 running between reagent reservoir 132 and analysis cell 101.

Preferably apparatus 10 also comprises a water device 120 for delivering purified water 121 from water reservoir 122 via pipe 123 to enable cell 101 to be rinsed between analyses, or water to be added to test solution 102. Preferably, computing device 151 with the stored algorithm is further operative to control water device 120.

Suitable reference electrodes and fluoride ion specific electrodes suitable for use in the apparatus of the invention are well-known in the art and are available commercially. Typical reference electrodes include the silver-silver chloride electrode (SSCE), saturated calomel electrode (SCE), mercury-mercury sulfate electrode, for example. A double junction may be used for one or both electrodes to minimize contamination of the electrode solution by etchant solution species (which may cause drift in the electrode potential). Fluoride ion specific electrode 141 and reference electrode 142 may be separate electrodes or may be combined in a combination electrode.

After a fluoride ISE measurement with the apparatus of the invention is completed, test solution 102 is preferably flowed via waste pipe 163 into waste container 162. Between silicon determinations, analysis cell 101 is preferably rinsed with water. Analysis cell 101 may be rinsed using water provided by water device 120 or by a separate rinse system (not shown). Waste 160 is disposed.

Fluoride ISE calibrations and measurements should be performed at a constant temperature, preferably at or near room temperature, and/or fluoride ISE potentials should be corrected for significant variations in the temperature of test solution 102. Preferably, the apparatus of the invention further comprises: a temperature sensor 170 for measuring the temperature of test solution 102. Temperature sensor 170 may be of any suitable type, including a thermometer, a thermocouple (as indicated in FIG. 1), a thermistor, or an NIR spectrometer, for example. Preferably, computing device 151 is further operative to acquire temperature data from the temperature sensor 170 and correct the potentials measured for fluoride ISE 141 for temperature effects so as to provide a more accurate determination of the fluoride concentration in test solution 102.

The apparatus of the invention preferably includes a means of controlling the temperature of test solution 102 to minimize errors in the measured concentration of fluoride ions in test solution 102. Suitable means of controlling the temperature of a liquid are well-known in the art. For example, a hot plate or an immersion heater with feedback from a temperature sensor may be used to control the temperature of a liquid in an analysis cell. A preferred means of controlling the temperature of test solution 102 is to pass water or another heat exchange liquid from a circulator/controller (or another constant temperature source) through a cooling jacket on analysis cell 101 (not shown).

Computing device 151 may comprise a computer with integrated components, or may comprise separate components, a microprocessor and a memory device that includes memory element 152, for example. Memory element 152 may be any one or a combination of available memory elements, including a computer hard drive, a microprocessor chip, a read-only memory (ROM) chip, a programmable read-only memory (PROM) chip, a magnetic storage device, a computer disk (CD) and a digital video disk (DVD), for example. Memory element 152 may be an integral part of computing device 151 or may be a separate device.

Description of a Preferred Embodiment

The efficacy of the invention for determining the concentration of silicon ions in an alkaline etchant solution comprising tetramethylammonium hydroxide (TMAH) was demonstrated. A hydroxide stock solution comprising 25 wt % TMAH in deionized water and a silicon stock solution comprising 5000 ppm silicon in deionized water were prepared. Note that the silicon stock solution was prepared by dissolving 98% sodium metasilicate nonahydrate ($Na_2SiO_3 \cdot 9H_2O$) but the concentration is given in terms of ppm (mg/kg) of elemental silicon (not the silicon compound).

Example 1

A first reagent solution comprising 20 wt. % $H_3PO_4$ and 2.30 g/L HF and a second reagent solution comprising 50 wt. % $H_3PO_4$ and 2.30 g/L HF were prepared by combining appropriate volumes of 85 wt. % phosphoric acid ($H_3PO_4$) solution, 49 wt. % hydrofluoric acid (HF) solution, and deionized water. A series of standard solutions comprising 5 wt. % tetramethylammonium hydroxide (TMAH) and 0, 50, 100, 150 or 200 ppm silicon were prepared by combining appropriate volumes of the silicon stock solution (5000 ppm), the hydroxide stock solution (25 wt % TMAH), and deionized water.

Measurements were performed using a combination FISE that included a silver-silver chloride electrode (SSCE) reference electrode (filled with 4 M KCl saturated with AgCl). The potential of the combination FISE in a 25-mL sample of each standard solution was measured initially and after each addition of a predetermined volume of the first reagent solution.

Table 1 summarizes the data obtained for calibration solutions (pH 2.1) resulting from addition of 0-13 mL of the first reagent solution (20 wt. % $H_3PO_4$ and 2.30 g/L HF) to 25 mL of each of the standard solutions comprising 5 wt. % TMAH. Since 9.36 mL of the first reagent solution is required to react with all of the silicon ions in the 200 ppm standard solution, the column for 10 mL of added reagent (bold type) in Table 1 provides data for calibration solutions for which the amount of fluoride ions is only 7.7% more than that needed to react with all of silicon ions in the 200 ppm standard solution. As indicated in Table 1, the measured silicon concentrations based on FISE potentials for calibration solutions comprising 10 mL of the first reagent solution are substantially equivalent to the actual values.

TABLE 1

Calibration Data for First Reagent Solution Comprising 20 wt. % Phosphoric Acid

| | | Reagent Added Silicon (ppm) | | | | | | | | | | |
|---|---|---|---|---|---|---|---|---|---|---|---|---|
| Actual | Measured | 0 mL | 2 mL | 4 mL | 6 mL | 7 mL | 8 mL | 9 mL | 10 mL | 11 mL | 12 mL | 13 mL |
| | | | | | | FISE Potential (mV vs. SSCE) | | | | | | |
| 0 | 2 | −466 | −477 | −496 | −493 | −493 | −473 | −463 | −456 | −451 | −447 | −444 |
| 50 | 49 | −462 | −480 | −497 | −477 | −460 | −452 | −447 | −443 | −440 | −438 | −435 |
| 100 | 96 | −464 | −481 | −497 | −461 | −434 | −433 | −432 | −430 | −429 | −428 | −427 |
| 150 | 151 | −467 | −481 | −498 | −455 | −426 | −417 | −414 | −415 | −418 | −419 | −419 |
| 200 | 201 | −468 | −481 | −498 | −452 | −422 | −411 | −406 | −402 | −402 | −404 | −407 |

Figure 2:
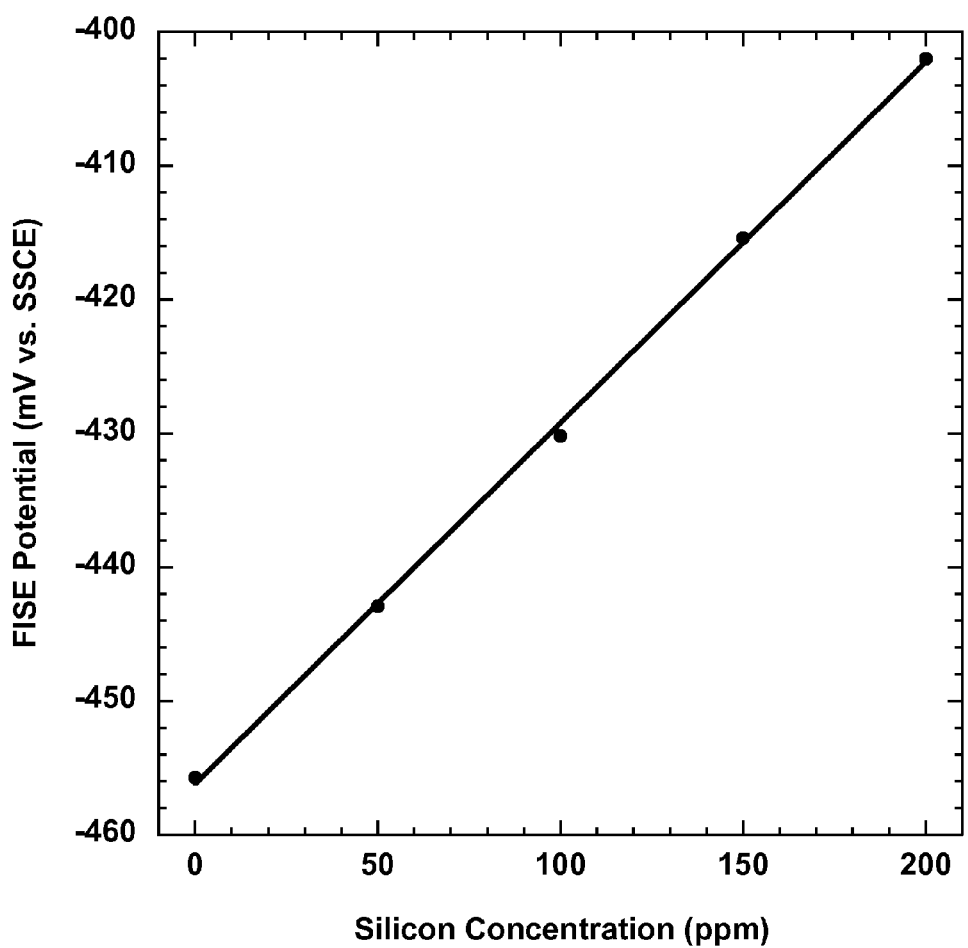
FIG. 2 is a calibration curve of the potential of a FISE in calibration solutions vs. the silicon concentration in the corresponding standard solutions (comprising 5 wt. % TMAH) to which 10 mL of a first reagent solution (comprising 20 wt. % phosphoric acid and 2.30 g/L HF) had been added to 25 mL of the standard solutions to provide calibration solutions.

FIG. 2 is a calibration curve of the potential of the FISE in the calibration solutions vs. the silicon concentration in the standard solutions (comprising 5 wt. % TMAH) to which 10 mL of the first reagent solution comprising 20 wt. % phosphoric acid and 2.30 g/L HF had been added to 25 mL of the standard solutions to provide the calibration solutions. This standard curve, which is highly linear and provides good sensitivity (0.27 mV/ppm) to the silicon concentration over the entire concentration range, represents a preferred embodiment of the invention for which the fluoride concentration is only slightly in excess of that required to react with all of the silicon ions at the maximum concentration (200 ppm) in the standard solutions. In this case, the calibration solution comprised 0.178 millimoles of silicon [(0.20 g/L)(0.025 L)(1000 millimoles/mole)/(28.1 g/mole)] and 1.15 millimoles of HF [(2.30 g/L)(0.010 L)(1000 millimoles/mole)/20 g/mole)], which is only 0.082 millimoles (7.7%) more than the 1.068 millimoles [(6 F/Si)(0.178 millimoles)] required for reaction with the 200 ppm silicon present in the standard solution.

Figure 3:
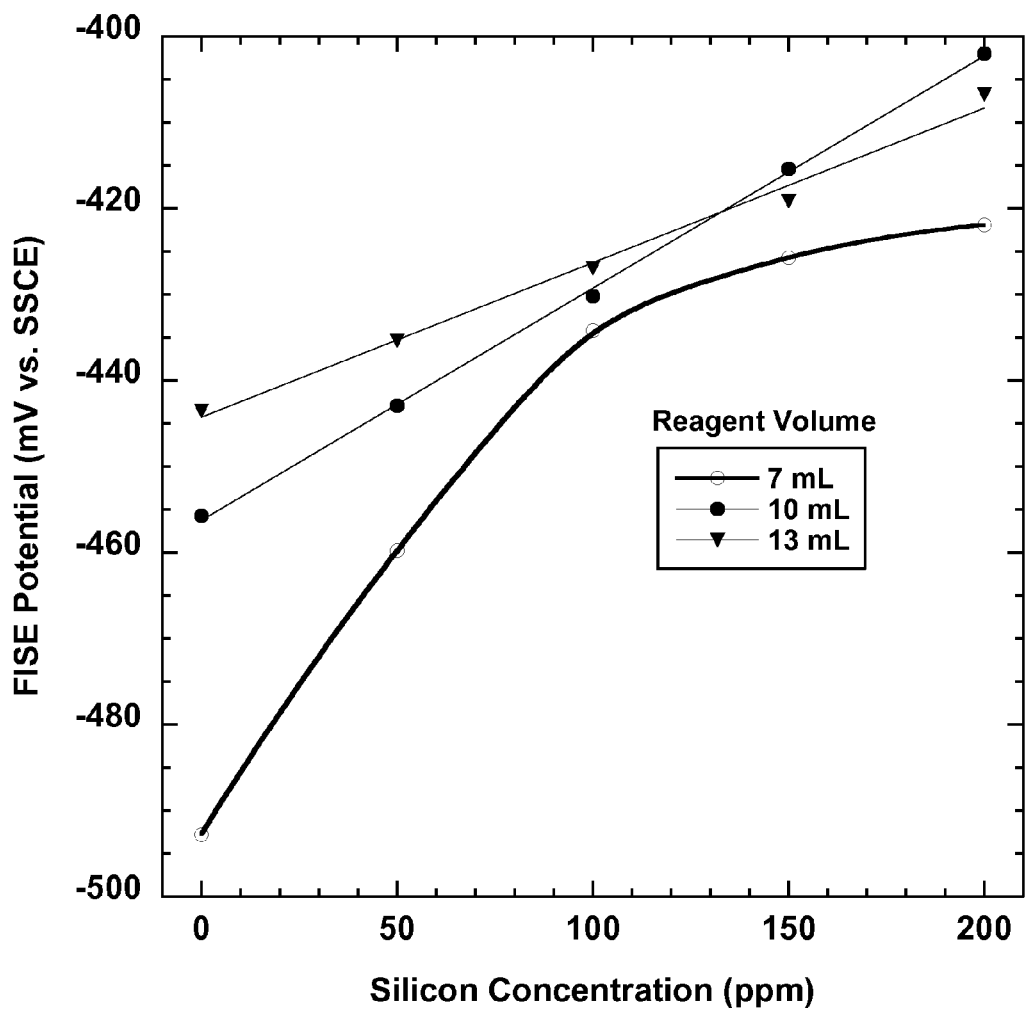
FIG. 3 shows plots of the potential of a FISE in calibration solutions vs. the silicon concentration in the corresponding standard solutions (comprising 5 wt. % TMAH) to which 7, 10 or 13 mL of a first reagent solution (comprising 20 wt. % phosphoric acid and 2.30 g/L HF) had been added to 25 mL of the standard solutions to provide calibration solutions.

FIG. 3 shows plots of the potential of the FISE in calibration solutions vs. the silicon concentration in the corresponding standard solutions (comprising 5 wt. % TMAH) to which 7, 10 or 13 mL of a first reagent solution (comprising 20 wt. % phosphoric acid and 2.30 g/L HF) had been added to 25 mL of the standard solutions to provide calibration solutions. The 10-mL plot is the linear calibration curve (from FIG. 2) for calibration solutions containing 1.15 millimoles HF, which is only 7.7% greater than that needed to react with the 1.068 millimoles of silicon present in the 200 ppm calibration solution.

For the 7-mL plot (FIG. 3), the amount of fluoride in the calibration solutions (0.805 millimoles) is 24.6% less than that needed to react with all of the silicon ions in the 200 ppm calibration solution (1.068 millimoles). In this case, the FISE potentials are generally lower and the plot is highly non-linear with a reduced slope at higher silicon concentrations (>100 ppm), which indicates reduced sensitivity to the silicon ions.

For the 13-mL plot (FIG. 3), the amount of fluoride in the calibration solutions (1.50 millimoles) is 40.0% more than that needed to react with all of the Si in the 200 ppm calibration solution (1.068 millimoles). In this case, the plot is linear but has a reduced slope, indicating a reduced sensitivity (0.19 mV/ppm) to the silicon ion concentration over the entire concentration range.

These data show that the calibration curve for 10 mL of added reagent solution (for which the amount of fluoride ion is only 7.7% more that that required to react with all of the silicon ions present in a 200 ppm standard solution) is optimum with respect to sensitivity (0.27 mV/ppm) to silicon ions over the entire silicon concentration range.

Figure 4:
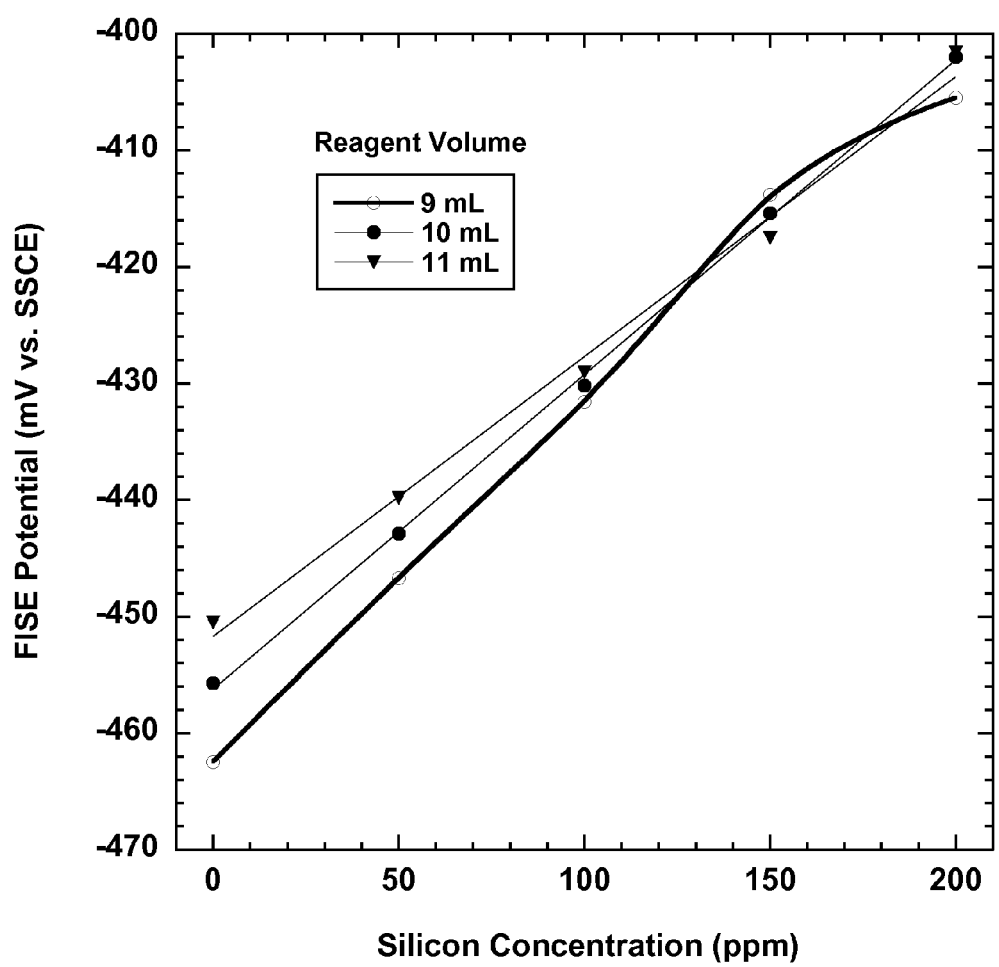
FIG. 4 shows plots of the potential of a FISE in calibration solutions vs. the silicon concentration in the corresponding standard solutions (comprising 5 wt. % TMAH) to which 9, 10 or 11 mL of a first reagent solution (comprising 20 wt. % phosphoric acid and 2.30 g/L HF) had been added to 25 mL of the standard solutions to provide calibration solutions.

FIG. 4 shows plots analogous to those of FIG. 3 but for addition of 9, 10 and 11 mL of the first reagent solution. In this case, the trends observed for the 7-mL and 13-mL plots (FIG. 3) are still evident but are less pronounced, as expected. The sensitivity for the 11-mL plot is 0.25 mV/ppm compared to 0.27 mV/ppm for the 10-mL solution.

Table 2 summarizes the data obtained for calibration solutions resulting from addition of 8-11 mL of the second reagent solution (50 wt. % $H_3PO_4$ and 2.30 g/L HF) to 25 mL of each of the standard solutions comprising 5 wt. % TMAH. As was the case for the reagent solution comprising 20 wt. % phosphoric acid, the column for 10 mL of added reagent (bold type) in Table 2 provides data for calibration solutions for which the amount of fluoride ions is only slightly in excess of that needed to react with all of silicon ions in the 200 ppm standard solution. As indicated in Table 2, the measured silicon concentrations based on FISE potentials for calibration solutions comprising 10 mL of the first reagent solution are substantially equivalent to the actual values.

TABLE 2

Calibration Data for Second Reagent Solution Comprising 50 wt. % Phosphoric Acid

| Silicon (ppm) | | Reagent Added | | | |
|---|---|---|---|---|---|
| | | 8 mL | 9 mL | 10 mL | 11 mL |
| Actual | Measured | FISE Potential (mV vs. SSCE) | | | |
| 0 | 2 | −378 | −377 | −376 | −374 |
| 50 | 49 | −368 | −369 | −368 | −368 |
| 100 | 96 | −355 | −357 | −358 | −359 |
| 150 | 151 | −346 | −345 | −346 | −348 |
| 200 | 201 | −342 | −339 | −338 | −337 |

Figure 5:
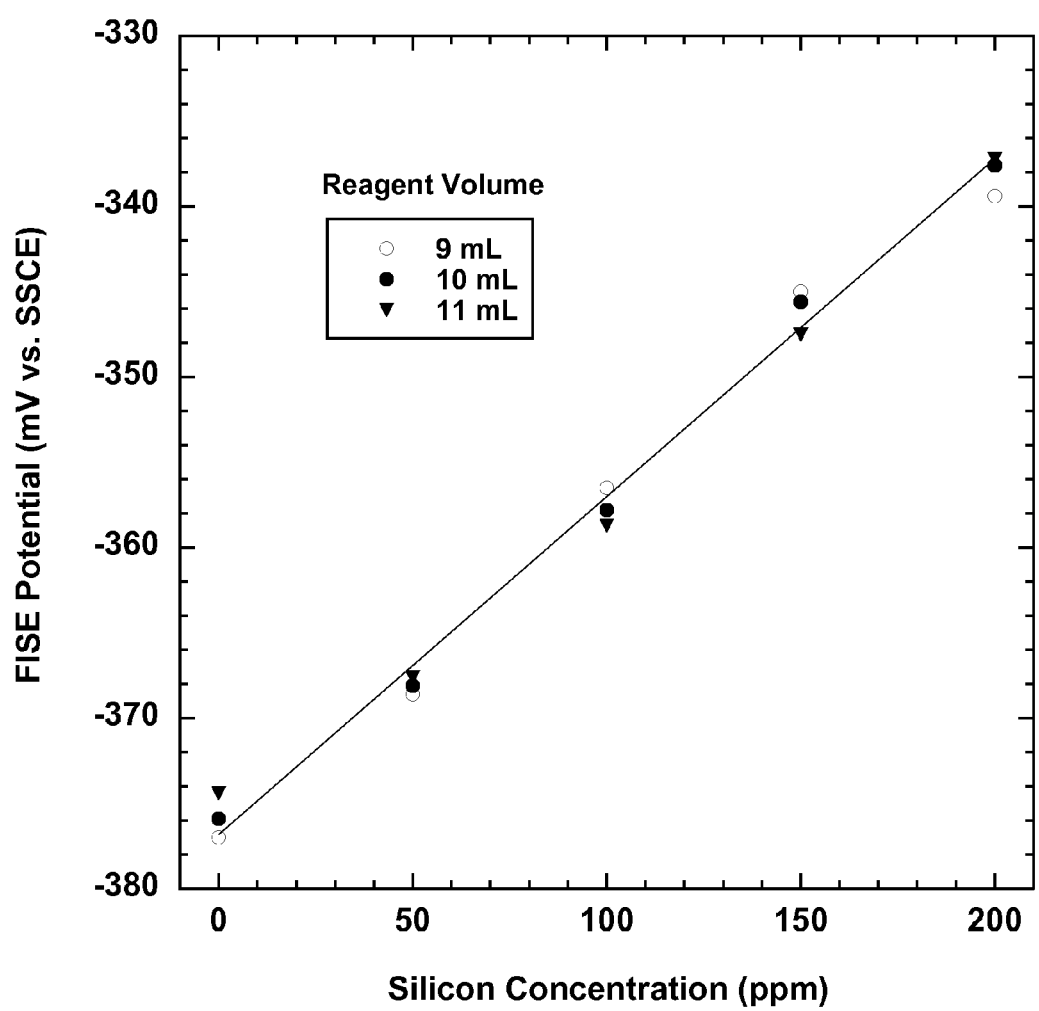
FIG. 5 shows calibration curves of the potential of a FISE in calibration solutions vs. the silicon concentration in the corresponding standard solutions (comprising 5 wt. % TMAH) to which 9, 10 or 11 mL of a second reagent solution (comprising 50 wt. % phosphoric acid and 2.30 g/L HF) had been added to 25 mL of the standard solutions to provide calibration solutions.

FIG. 5 shows plots analogous to those of FIG. 4 for a second reagent solution comprising 50 wt. % phosphoric acid (and 2.30 g/L HF) instead of 20 wt. % phosphoric acid (and 2.30 g/L HF) so that the calibration solutions were more acidic (pH 0.9). In this case, the calibration curve for addition of 10 mL of the second reagent solution exhibited somewhat more scatter and a lower sensitivity (0.20 mV/ppm) to the silicon ions than observed for addition of 10 mL of the first reagent solution, but the deviations for the 9 and 10-mL plots are less pronounced.

Figure 6:
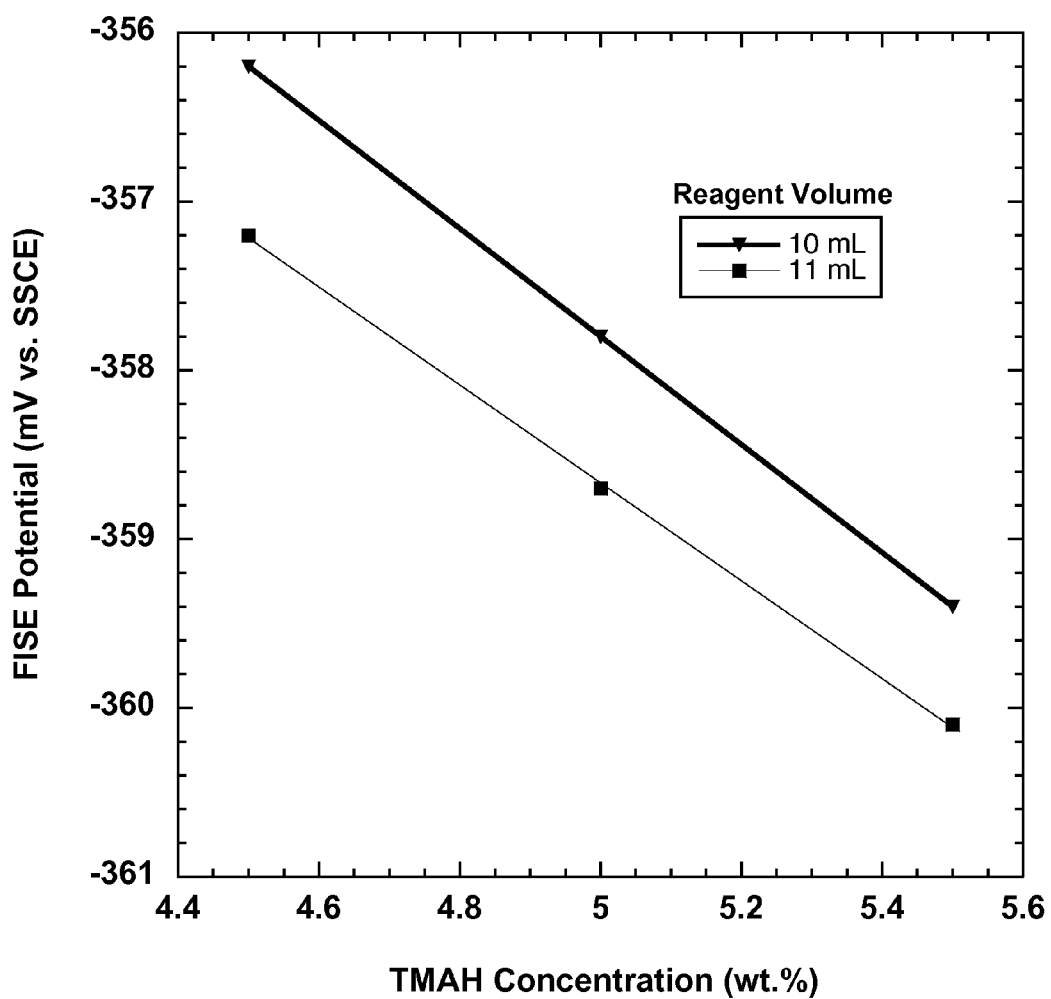
FIG. 6 shows plots of the potential of a FISE in calibration solutions vs. the TMAH concentration in the corresponding standard solutions to which 8, 9, 10 or 11 mL of a second reagent solution (comprising 50 wt. % phosphoric acid and 2.30 g/L HF) had been added to 25 mL of the standard solutions to provide the calibration solutions.

FIG. 6 shows plots of the potential of the FISE in calibration solutions vs. the TMAH concentration in the corresponding standard solutions to which 10 or 11 mL of a second reagent solution (comprising 50 wt. % phosphoric acid and 2.30 g/L HF) had been added to 25 mL of the standard solutions to provide the calibration solutions. From the slopes of these plots (3.2 and 2.9 mV/wt. % TMAH) and the slope of the calibration curve in FIG. 5 (0.2 mV/ppm), a change in the TMAH concentration of 1.0% would introduce an error of about 15 ppm for the silicon concentration measured with a reagent comprising 50 wt. % $H_3PO_4$ (and 2.30 g/L HF) for an etchant solution comprising 5 wt. % TMAH. Typically, the concentration of the hydroxide compound in production etchant solutions is closely controlled so that actual errors should be small. If necessary, the measured FISE potentials may be corrected for variations in the etchant solution hydroxide concentration.

These examples illustrate key features of the invention for determining the silicon concentration in an alkaline etching solution by measuring the potential of a fluoride ion specific electrode (FISE) in a test solution comprising a sample of the alkaline etching solution, an acid added to provide a pH in a predetermined pH range, and an amount of fluoride ions in stoichiometric excess of that required to react with all of the silicon ions at a maximum expected concentration in the alkaline etchant solution. For these examples, optimum results were obtained by using a relatively acidic test solution (pH 0.9-1.1), only a small stoichiometric excess of fluoride ions (0-10%), and an analysis range limited to the maximum expected silicon concentration in the alkaline etchant solution. Acceptable results according to the invention may be provided for some alkaline etchant solutions, some etchant products and some applications using a wider pH range (0.0-3.0) and a greater stoichiometric excess of fluoride ions (up to at least 30%).

The preferred embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A method of determining a concentration of an etchant product in an alkaline etchant solution comprising a predetermined concentration of a hydroxide compound dissolved in water, comprising the steps of:
    defining a maximum expected concentration of the etchant product in the alkaline etchant solution;
    providing a plurality of standard solutions comprising the predetermined concentration of the hydroxide compound and different predetermined concentrations of the etchant product in a range from zero to a maximum expected concentration of the etchant product in the alkaline etchant solution;

adding predetermined concentrations of an acid and fluoride ions to each of the standard solutions to provide a plurality of calibration solutions having a pH in the 0.0-3.0 pH range and a concentration of fluoride ions in stoichiometric excess of that required to react with all of the etchant product in an alkaline etchant solution comprising the maximum expected concentration of the etchant product;

generating a calibration curve of a concentration of the etchant product versus a potential of a fluoride ion specific electrode (FISE) by sequentially placing the FISE and a reference electrode in contact with each calibration solution and measuring the potential of the FISE relative to the reference electrode via a voltmeter;

providing a test solution comprising a predetermined volume of the alkaline etchant solution and the same predetermined concentrations of the acid and fluoride ions as in the calibration solutions;

placing the FISE and the reference electrode in contact with the test solution and measuring the potential of the FISE relative to the reference electrode via the voltmeter; and comparing the potential of the FISE measured for the test solution with the calibration curve to determine the concentration of the etchant product in the alkaline etchant solution, wherein fluoride ions are added to the test solution and the calibration solutions as part of a fluoride compound, and the FISE and the reference electrode may be separate electrodes or may be combined in a combination electrode.

2. The method of claim 1, wherein the etchant product comprises ions of an element selected from the group consisting of silicon, germanium and titanium.

3. The method of claim 1, wherein the hydroxide compound is selected from the group consisting of tetramethylammonium hydroxide (TMAH), tetraethylammonium hydroxide (TEAH), tetrapropylammonium hydroxide (TPAH), tetrabuytlammonium hydroxide (TBAH), NaOH, KOH and mixtures thereof.

4. The method of claim 1, wherein the maximum expected concentration of the etchant product in the alkaline etchant solution is defined based on measurements of the etchant product concentration in a production alkaline etchant solution as a function of time, or by a process control document specifying a maximum allowable concentration of the etchant product.

5. The method of claim 1, wherein the acid is selected from the group consisting of phosphoric acid, sulfuric acid, nitric acid, acetic acid, hydrochloric acid and mixtures thereof.

6. The method of claim 1, wherein the fluoride compound is selected from the group consisting of HF, LiF, NaF, KF, $NH_4HF_2$, $NH_4F$, and mixtures thereof.

7. The method of claim 1, wherein the stoichiometric excess of fluoride ions is less than 30% of the fluoride ion concentration required to react with all of the etchant product in an alkaline etchant solution comprising the maximum expected concentration of the etchant product.

8. The method of claim 1, further comprising the step of:
providing a reagent solution comprising a predetermined concentration of the acid and a predetermined concentration of fluoride ions,
whereby the predetermined concentrations of the acid and fluoride ions are added to the calibration solutions and the test solution.

9. The method of claim 1, wherein a free fluoride ion concentration is determined from the FISE potential measured for each of the calibration solutions and the test solution and used to calculate the concentration of the etchant product.

10. The method of claim 1, further comprising the steps of:
maintaining a temperature of the calibration solutions substantially constant at a predetermined calibration temperature during FISE potential measurements for the calibration solutions;
measuring the temperature of the test solution at a time the FISE potential is measured for the test solution; and
correcting the potential measured for the FISE in the test solution for the effect of a difference in the temperature measured for the test solution and the predetermined calibration temperature.

11. The method of claim 1, wherein the measured FISE potentials are corrected for variations in the concentration of the hydroxide compound in the alkaline etchant solution.

12. A method of determining a concentration of silicon ions in an alkaline etchant solution comprising a predetermined concentration of a hydroxide compound dissolved in water, comprising the steps of:
defining a maximum expected concentration of the silicon ions in the alkaline etchant solution;
providing a reagent solution comprising a predetermined concentration of phosphoric acid and a predetermined concentration of fluoride ions;
providing a plurality of standard solutions comprising the predetermined concentration of the hydroxide compound and different predetermined concentrations of silicon ions in a range from zero to the maximum expected concentration of silicon ions in the alkaline etchant solution;
adding a predetermined volume fraction of the reagent solution to each of the standard solutions to provide a plurality of calibration solutions, and to a sample of the alkaline etchant solution to provide a test solution;
generating a calibration curve of the concentration of silicon ions in the etchant solution versus a potential of a fluoride ion specific electrode (FISE) by sequentially placing the FISE and a reference electrode in contact with each calibration solution and measuring the potential of the FISE relative to the reference electrode via a voltmeter;
placing the FISE and the reference electrode in contact with the test solution and measuring the potential of the FISE relative to the reference electrode via the voltmeter; and
comparing the potential of the FISE measured for the test solution with the calibration curve to determine the concentration of silicon ions in the alkaline etchant solution,
wherein fluoride ions are added to the reagent solution as part of a fluoride compound,
the predetermined concentration of phosphoric acid in the reagent solution provides a pH for the calibration and test solutions in a 0.0-3.0 pH range,
the predetermined concentration of fluoride ions in the reagent solution provides a concentration of fluoride ions in the calibration and test solutions in excess of that required for complete reaction with all of the silicon ions at the maximum expected concentration in the alkaline etchant solution, and
the FISE and the reference electrode may be separate electrodes or may be combined in a combination electrode.

13. The method of claim 12, wherein the hydroxide compound is selected from the group consisting of tetramethylammonium hydroxide (TMAH), tetraethylammonium hydroxide (TEAH), tetrapropylammonium hydroxide (TPAH), tetrabuytlammonium hydroxide (TBAH), NaOH, KOH and mixtures thereof.

14. The method of claim 12, wherein the fluoride compound is selected from the group consisting of HF, LiF, NaF, KF, $NH_4HF_2$, $NH_4F$, and mixtures thereof.

* * * * *